United States Patent
Eisaman (10) Patent No.: US 9,914,683 B2
(45) Date of Patent: Mar. 13, 2018

(54) FUEL SYNTHESIS FROM AN AQUEOUS SOLUTION

(71) Applicant: X Development LLC, Mountain View, CA (US)

(72) Inventor: Matthew D. Eisaman, Port Jefferson, NY (US)

(73) Assignee: X Development LLC, Mountain View, CA (US)

(*) Notice: Subject to any disclaimer, the term of this patent is extended or adjusted under 35 U.S.C. 154(b) by 0 days.

(21) Appl. No.: 15/165,357

(22) Filed: May 26, 2016

(65) Prior Publication Data

US 2017/0342004 A1 Nov. 30, 2017

(51) Int. Cl.
| | |
|---|---|
| C07C 29/152 | (2006.01) |
| C07C 41/09 | (2006.01) |
| C10G 2/00 | (2006.01) |
| C25B 1/04 | (2006.01) |
| C01B 3/06 | (2006.01) |

(Continued)

(52) U.S. Cl.
CPC .............. *C07C 29/152* (2013.01); *C01B 3/06* (2013.01); *C01B 31/20* (2013.01); *C07C 29/1518* (2013.01); *C07C 41/09* (2013.01); *C10G 2/30* (2013.01); *C10G 2/50* (2013.01); *C10L 1/02* (2013.01); *C10L 1/04* (2013.01);
(Continued)

(58) Field of Classification Search
CPC ................ B01D 53/62; B01D 2251/30; B01D 2257/504; B01D 2259/4558; Y02C 10/04; C07C 1/20; C07C 29/149; C07C 41/09; C07C 67/36; C07C 11/02; C07C 43/043; C07C 31/04

See application file for complete search history.

(56) References Cited

U.S. PATENT DOCUMENTS

| | | |
|---|---|---|
| 3,075,828 A | 1/1963 | Kato et al. |
| 3,627,479 A | 12/1971 | Yee |

(Continued)

FOREIGN PATENT DOCUMENTS

| | | |
|---|---|---|
| CN | 102936067 A | 2/2013 |
| EP | 1276795 | 3/2006 |

(Continued)

OTHER PUBLICATIONS

Willauer, H. D. et al., Extraction of Carbon Dioxide from Seawater by an Electrochemical Acidification Cell. Part 2—Laboratory Scaling Studies, Apr. 2011, 22 pages.

(Continued)

*Primary Examiner* — Jafar Parsa
(74) *Attorney, Agent, or Firm* — Christensen O'Connor Johnson Kindness PLLC (57) ABSTRACT

A method of synthesizing fuel from an aqueous solution includes pumping the aqueous solution, containing dissolved inorganic carbon, from a body of water into a carbon extraction unit. The method further includes extracting the dissolved inorganic carbon from the aqueous solution to create $CO_2$ by changing a pH of the aqueous solution in the carbon extraction unit. The $CO_2$ derived in the carbon extraction unit is received by a fuel synthesis unit, and the $CO_2$ is converted into fuel including at least one of a hydrocarbon, an ether, or an alcohol using the fuel synthesis unit.

20 Claims, 6 Drawing Sheets

(51) Int. Cl.
*C07C 29/151* (2006.01)
*C10L 1/02* (2006.01)
*C10L 1/04* (2006.01)
*C01B 31/20* (2006.01)

(52) U.S. Cl.
CPC ............ *C25B 1/04* (2013.01); *C10L 2290/38* (2013.01); *C10L 2290/42* (2013.01); *C10L 2290/544* (2013.01)

(56) References Cited

U.S. PATENT DOCUMENTS

| | | |
|---|---|---|
| 4,036,749 A | 7/1977 | Anderson |
| 4,392,959 A | 7/1983 | Coillet |
| 6,905,606 B1 | 6/2005 | Kikuyama et al. |
| 7,117,106 B2 | 10/2006 | Rusta-Sallehy et al. |
| 7,198,722 B2 | 4/2007 | Hussain |
| 7,655,193 B1 | 2/2010 | Rau et al. |
| 7,700,214 B1 | 4/2010 | Iyer et al. |
| 7,906,028 B2 | 3/2011 | Constantz et al. |
| 7,931,809 B2 | 4/2011 | Constantz et al. |
| 7,947,239 B2 | 5/2011 | Lackner et al. |
| 8,227,127 B2 | 7/2012 | Little et al. |
| 8,313,557 B2 | 11/2012 | Willauer et al. |
| 8,337,589 B2 | 12/2012 | Wright et al. |
| 8,685,250 B2 | 4/2014 | Choi et al. |
| 8,778,156 B2 | 7/2014 | Eisaman et al. |
| 8,784,632 B2 | 7/2014 | Eisaman et al. |
| 8,999,171 B2 | 4/2015 | Wallace |
| 9,227,168 B1 | 1/2016 | DeVaul et al. |
| 9,403,698 B2 | 8/2016 | Dennis et al. |
| 2005/0074657 A1 | 4/2005 | Rusta-Sallehy et al. |
| 2008/0033338 A1 | 2/2008 | Smith |
| 2008/0039538 A1* | 2/2008 | Olah .................. C07C 1/20 518/702 |
| 2008/0093307 A1 | 4/2008 | Somers et al. |
| 2009/0001020 A1 | 1/2009 | Constantz et al. |
| 2010/0028242 A1 | 2/2010 | Willauer et al. |
| 2010/0233767 A1 | 9/2010 | McMurran |
| 2010/0288700 A1 | 11/2010 | Lahav et al. |
| 2011/0056876 A1 | 3/2011 | Ide et al. |
| 2011/0135551 A1 | 6/2011 | House et al. |
| 2011/0177550 A1 | 7/2011 | McMurran |
| 2011/0206566 A1 | 8/2011 | Stoots et al. |
| 2011/0224578 A1 | 9/2011 | Edman et al. |
| 2011/0226006 A1 | 9/2011 | Lackner et al. |
| 2011/0237839 A1 | 9/2011 | Waldstein |
| 2011/0281959 A1 | 11/2011 | DiMascio et al. |
| 2012/0201717 A1 | 8/2012 | Singh et al. |
| 2012/0211421 A1 | 8/2012 | Self et al. |
| 2012/0220019 A1 | 8/2012 | Lackner |
| 2012/0244053 A1 | 9/2012 | Self et al. |
| 2013/0008792 A1 | 1/2013 | Eisaman et al. |
| 2013/0034760 A1 | 2/2013 | Otts et al. |
| 2013/0206605 A1 | 8/2013 | DiMascio et al. |
| 2013/0281553 A1 | 10/2013 | Kubic et al. |
| 2013/0343981 A1 | 12/2013 | Wright et al. |
| 2014/0002788 A1 | 1/2014 | Otts et al. |
| 2014/0217024 A1 | 8/2014 | Monzyk et al. |
| 2014/0234735 A1 | 8/2014 | Zhang et al. |
| 2014/0238869 A1 | 8/2014 | DiMascio et al. |
| 2014/0272639 A1 | 9/2014 | Zietlow |
| 2014/0303452 A1 | 10/2014 | Ghaffari |
| 2014/0322803 A1 | 10/2014 | Constantz et al. |
| 2014/0338903 A1 | 11/2014 | Mahmoud et al. |
| 2015/0274536 A1 | 10/2015 | Wright et al. |
| 2015/0298806 A1 | 10/2015 | Lind et al. |
| 2016/0082387 A1 | 3/2016 | Constantz et al. |
| 2016/0311701 A1 | 10/2016 | Dennis et al. |

FOREIGN PATENT DOCUMENTS

| | | |
|---|---|---|
| EP | 2074066 | 7/2009 |
| EP | 2465600 | 6/2012 |
| EP | 2465601 | 6/2012 |
| EP | 2543427 | 1/2013 |
| WO | WO 9412465 | 6/1994 |
| WO | WO 2010/142943 A2 | 12/2010 |
| WO | WO 2011/090376 A1 | 7/2011 |

OTHER PUBLICATIONS

Eisaman M. D. et al., CO2 extraction from seawater using bipolar membrane electrodialysis, May 2012, 8 pages.
Biorock International Coral Reef Restoration, Biorock International Corporation, 2012, 2 pages.
Rangel C. M. et al., Integrating hydrogen generation and storage in a novel compact electrochemical system based on metal hydrides, Jul. 2008, 5 pages.
U.S. Appl. No. 62/342,061—Method for Efficient CO2 Degasification, filed May 26, 2016, 23 pages.
U.S. Appl. No. 15/165,867—Method for Feeding Algae Using Reclaimed CO2, filed May 26, 2016, 19 pages.
U.S. Appl. No. 15/165,885—Metal Hydride Electrolysis System, filed May 26, 2016, 21 pages.
U.S. Appl. No. 62/342,065—Chemical Extraction From an Aqueous Solution, filed May 26, 2016, 29 pages.
U.S. Appl. No. 15/165,205—Chemical Extraction From an Aqueous Solution and Power Generator Cooling, filed May 26, 2016, 30 pages.
U.S. Appl. No. 15/165,260—Building Materials From an Aqueous Solution, filed May 26, 2016, 29 pages.
U.S. Appl. No. 15/165,311—Enhanced Hydrocarbon Extraction, filed May 26, 2016, 27 pages.
Eisaman M. D. et al., CO2 separation using bipolar membrane electrodialysis, Energy & Environmental Science, Apr. 2011, 10 pages.
U.S. Appl. No. 14/971,122—Electrodialytic CO2 Purification and Stripping, filed Dec. 16, 2015, 16 pages.
U.S. Appl. No. 14/736,847—Energy Efficient Method for Stripping CO2 From Seawater, filed Jun. 11, 2015, 16 pages.
U.S. Appl. No. 14/750,800—CO2 Sequestration via Desalination, filed Jun. 25, 2015, 16 pages.
International Search Report and Written Opinion from the International Searching Authority dated Aug. 18, 2017, for International Application No. PCT/US2017/031519, filed May 8, 2017, 13 pages.

* cited by examiner

FUEL SYNTHESIS FROM AN AQUEOUS SOLUTION

TECHNICAL FIELD

This disclosure relates generally to fuel synthesis.

BACKGROUND INFORMATION

Pure carbon dioxide ($CO_2$) has many industrial uses. The separation of $CO_2$ from a mixed-gas source may be accomplished by a capture and regeneration process. More specifically, the process generally includes a selective capture of $CO_2$, by, for example, contacting a mixed-gas source with a solid or liquid adsorber/absorber followed by a generation or desorption of $CO_2$ from the adsorber/absorber. One technique describes the use of bipolar membrane electrodialysis for $CO_2$ extraction/removal from potassium carbonate and bicarbonate solutions.

For capture/regeneration systems, a volume of gas that is processed is generally inversely related to a concentration of $CO_2$ in the mixed-gas source, adding significant challenges to the separation of $CO_2$ from dilute sources such as the atmosphere. $CO_2$ in the atmosphere, however, establishes equilibrium with the total dissolved inorganic carbon in the oceans, which is largely in the form of bicarbonate ions ($HCO_3$—) at an ocean pH of 8.1-8.3. Therefore, a method for extracting $CO_2$ from the dissolved inorganic carbon of the oceans would effectively enable the separation of $CO_2$ from atmosphere without the need to process large volumes of air.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus and method for synthesizing fuel from an aqueous solution are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Throughout the specification and claims, compounds/elements are referred to both by their chemical name (e.g., carbon dioxide) and chemical symbol (e.g., $CO_2$). It is appreciated that both chemical names and symbols may be used interchangeably and have the same meaning.

This disclosure provides for the removal of carbon from water sources containing dissolved inorganic carbon (e.g., bicarbonate ions $HCO_3^-$), converting the dissolved carbon into $CO_2$ gas, and processing the $CO_2$ gas to produce alcohol, ether or hydrocarbon based fuels. The ability to produce alcohol, ether, and hydrocarbon fuel from nothing more than seawater is highly desirable in many industries. For example, a ship capable of making fuels from seawater could sail the oceans refueling airplanes on its own deck and/or refueling other ships without docking in port. Also, remote or isolated islands or coastal communities could make their own liquid fuels from seawater and electricity without the need for imported fuel delivery. Furthermore, the system and method for fuel synthesis presented here is carbon neutral (if powered with carbon-free electricity) because the elemental constituents of the hydrocarbons/ethers/alcohols formed are extracted from the ocean. Thus, there is no net carbon emission.

Figure 1A:
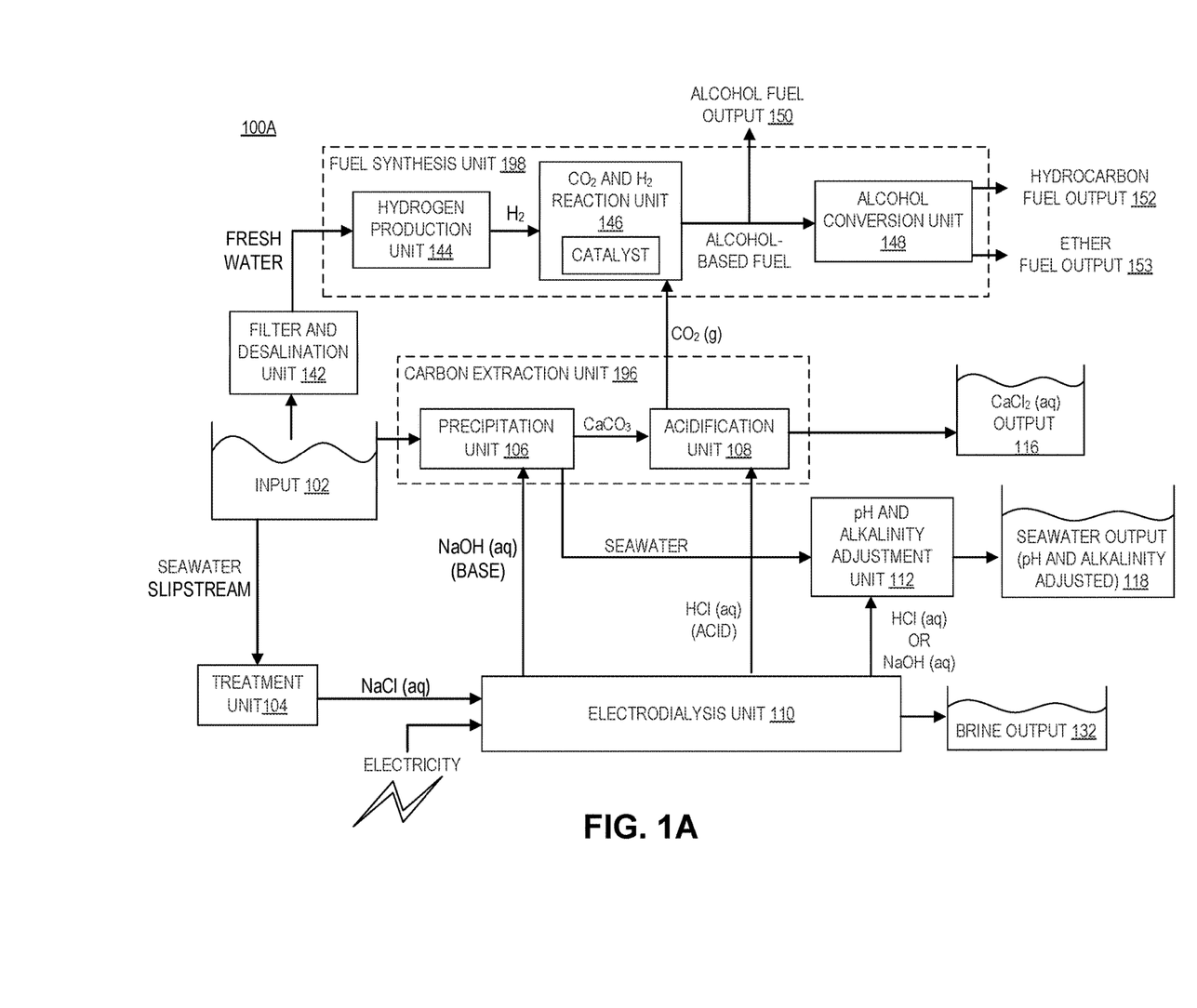
FIG. 1A is an illustration of a system for fuel synthesis, in accordance with an embodiment of the disclosure.

FIG. 1A is an illustration of system 100A for fuel synthesis, in accordance with an embodiment of the disclosure. System 100A includes: input 102 (to input an aqueous solution containing dissolved inorganic carbon), treatment unit 104, carbon extraction unit 196 (including precipitation unit 106 and acidification unit 108), electrodialysis unit 110, pH and alkalinity adjustment unit 112, $CaCl_2$ output 116, water output 118, brine output 132, filter and desalination unit 142, and fuel synthesis unit 198. In the depicted embodiment, fuel synthesis unit 198 includes: hydrogen production unit 144, $CO_2$ and $H_2$ reaction unit 146, alcohol conversion unit 148, alcohol fuel output 150, hydrocarbon fuel output 152, and ether fuel output 153.

As shown, input 102 is coupled to a water reservoir containing dissolved inorganic carbon (e.g., bicarbonate ions). The water reservoir may be an ocean, lake, river, manmade reservoir, or brine outflow from a reverse osmosis ("RO") process. Input 102 may receive the water through a system of channels, pipes, and/or pumps depending on the specific design of the facility. As shown, water received through input 102 is diverted into three separate sections of system 100A. A first (smaller) portion of the water is diverted to treatment unit 104, a second (larger) portion of the water is diverted to precipitation unit 106, and a third (smaller) portion of water is diverted to filter and desalination unit 142. In one embodiment, the inputs to filter and desalination unit 142 and treatment unit 104 may come from the output of pH and alkalinity adjustment unit 112, since the output of pH and alkalinity adjustment unit 112 has already been pre-softened via $CaCO_3$ removal in precipitation unit 106. One skilled in the art will appreciate that large aggregate may be removed from the water at any time during the intake process.

In the illustrated embodiment, the first portion of water is diverted into treatment unit 104. Treatment unit 104 outputs a relatively pure stream of aqueous NaCl. In other words, an aqueous solution (possibly including seawater) is input to treatment unit 104, and aqueous NaCl is output from treatment unit 104. Treatment unit 104 may be used to remove organic compounds and other minerals (other than NaCl) not needed in, or harmful to, subsequent processing steps. For example, removal of chemicals in the water may mitigate scale buildup in electrodialysis unit 110. Treatment unit 104 may include filtering systems such as: nanofilters, RO units, ion exchange resins, precipitation units, microfilters, screen filters, disk filters, media filters, sand filters, cloth filters, and biological filters (such as algae scrubbers), or the like. Additionally, treatment unit 104 may include chemical filters to removed dissolved minerals/ions. One skilled in the art will appreciate that any number of screening and/or filtering methods may be used by treatment unit 104 to remove materials, chemicals, aggregate, biologicals, or the like.

Electrodialysis unit 110 is coupled to receive aqueous NaCl and electricity, and output aqueous HCl, aqueous NaOH, and brine (to brine output 132). Aqueous HCl and aqueous NaOH output from electrodialysis unit 110 may be used to drive chemical reactions in system 100A. The specific design and internal geometry of electrodialysis unit 110 is discussed in greater detail in connection with FIG. 2 (see infra FIG. 2). Brine output from electrodialysis unit 110 may be used in any applicable portion of system 100A. For example, brine may be cycled back into electrodialysis unit 110 as a source of aqueous NaCl, or may be simply expelled from system 100A as wastewater.

In the depicted embodiment, carbon extraction unit 196 includes precipitation unit 106 and acidification unit 108. Precipitation unit 106 has a first input coupled to receive an aqueous solution including dissolved inorganic carbon (e.g., seawater) from input 102. Precipitation unit 106 also has a second input coupled to electrodialysis unit 110 to receive aqueous NaOH. In response to receiving the aqueous solution and the aqueous NaOH, precipitation unit 106 precipitates calcium salts (for example, but not limited to, $CaCO_3$) and outputs the aqueous solution. However, in other embodiments, other chemical processes may be used to basify the aqueous solution in precipitation unit 106. For example, other bases (not derived from the input aqueous solution) may be added to the aqueous solution to precipitate calcium salts.

In one embodiment, NaOH is added to incoming seawater until the pH is sufficiently high to allow precipitation of calcium salts without significant precipitation of $Mg(OH)_2$. The exact pH when precipitation of $CaCO_3$ occurs (without significant precipitation of $Mg(OH)_2$) will depend on the properties of the incoming seawater (alkalinity, temperature, composition, etc.); however, a pH of 9.3 is typical of seawater at a temperature of 25° C. In a different embodiment, the quantity of NaOH added is sufficient to precipitate $CaCO_3$ and $Mg(OH)_2$, then the pH is lowered (e.g., by adding HCl from electrodialysis unit 110 until the pH is <9.3) so that the $Mg(OH)_2$ (but not $CaCO_3$) redissolves.

In one embodiment, precipitation unit 106 may be a large vat or tank. In other embodiments precipitation unit 106 may include a series of ponds/pools. In this embodiment, precipitation of calcium salts may occur via evaporation driven concentration (for example using solar ponds) rather than, or in combination with, adding basic substances. Precipitation unit 106 may contain internal structures with a high surface area to promote nucleation of $CaCO_3$; these high surface area structures may be removed from the precipitation unit 106 to collect nucleated $CaCO_3$. Precipitation unit 106 may include an interior with $CaCO_3$ to increase nucleation kinetics by supplying seed crystals. The bottom of precipitation unit 106 may be designed to continually collect and extract precipitate to prevent large quantities of scale buildup.

In another or the same embodiment, heat may be used to aid precipitation. For example solar ponds may be used to heat basified water. In continuously flowing systems, low temperature waste heat solution may be flowed through heat exchange tubes with basified seawater on the outside of the tubes. Alternatively, heating the bottom of precipitation unit 106 may be used to speed up precipitation.

After $CaCO_3$ is precipitated from the water, $CaCO_3$ is transferred to acidification unit 108. In the depicted embodiment, acidification unit 108 is coupled to receive $CaCO_3$ from precipitation unit 106 and coupled to receive aqueous HCl from electrodialysis unit 110. In response to receiving $CaCO_3$ and aqueous HCl, acidification unit 108 produces $CO_2$ gas. In the depicted embodiment, acidification unit 108 is used to evolve $CaCO_3$ into $CO_2$ gas and aqueous $CaCl_2$ according to the following reaction: $CaCO_3$ (s)+2HCl (aq) →$CaCl_2$ (aq)+$H_2O$ (l)+$CO_2$ (g). Reaction kinetics may be increased by agitating/heating the acidified mixture. By adding HCl to $CaCO_3$, $CO_2$ gas is spontaneously released due to the high equilibrium partial pressure of $CO_2$ gas. This may eliminate the need for membrane contactors or vacuum systems.

Once all $CO_2$ has been extracted from acidification unit 108, wastewater containing $CaCl_2$ is output from system 100A via $CaCl_2$ output 116. In one embodiment, the wastewater is returned to the ocean or other water source after the pH of the wastewater has been adjusted.

In the depicted embodiment, the second portion of seawater (that was used as a carbon source in precipitation unit 106) is flowed to a pH and alkalinity adjustment unit 112. The pH and alkalinity adjustment unit 112 is coupled to electrodialysis unit 110 to receive HCl and NaOH, and adjust a pH and alkalinity of the combined second portion of the aqueous solution and basic solution to a desired pH and alkalinity. In one embodiment, the pH and alkalinity of wastewater flowed into pH and alkalinity adjustment unit 112 is monitored in real time, and HCl or NaOH is flowed into pH and alkalinity adjustment unit 112 in response to the real time measurements. Adjusting the pH of wastewater flowing from system 100A ensures minimal environmental impact of running system 100A, while adjusting the alkalinity ensures sufficient reabsorption of atmospheric $CO_2$ once the water is returned to the ocean.

As shown, input 102 is also coupled to send water to filter and desalination unit 142. Filter and desalination unit 142 removes aggregate and minerals from the water, thus the water leaving filter and desalination unit 142 is relatively pure fresh water. One skilled in the art will realize that a variety of commercial systems may be used to desalinate and purify water; many of these systems are already installed on commercial seafaring vessels.

Freshwater from filter and desalination unit 142 is then diverted into fuel synthesis unit 198. More specifically, in the depicted embodiment, the fresh water is sent to hydrogen production unit 144 which may separate hydrogen ($H_2$) from the fresh water via alkaline electrolysis, polymer electrolyte membrane electrolysis, solid oxide electrolysis, or the like.

O₂ resulting from the decomposition of the fresh water may be used in other chemical processes, or may simply be expelled from system 100A.

The $CO_2$ evolved from carbon extraction unit 196 and the $H_2$ produced by hydrogen production unit 144 is received by $CO_2$ and $H_2$ reaction unit 146. In the depicted embodiment, $CO_2$ and $H_2$ reaction unit 146 reacts the $CO_2$ with hydrogen to produce alcohol. In one embodiment, the alcohol includes methanol. In a different or the same embodiment, reacting the $CO_2$ with the hydrogen includes reacting the hydrogen and the $CO_2$ over a catalyst (e.g., Cu/ZnO, $AlO_x$, $GaO_x$, $ZrO_x$, $Cr_xO_x$, and other metal-oxide-based catalysts) to produce the methanol.

As shown, the derived alcohol can be output from the system via alcohol fuel output 150, or may be converted into hydrocarbon or ether fuel. As one skilled in the art will appreciate, alcohols, ethers, and hydrocarbons have many uses not limited to fuel. And while this disclosure refers to deriving "fuels" from $CO_2$, the alcohols, ethers, and hydrocarbons output from system 100A may be used for any reasonable purpose such as fuel additives, solvents, and feedstock for the conversion into other commodity chemicals and plastics, etc.

In the depicted embodiment, at least some of the alcohol generated by $CO_2$ and $H_2$ reaction unit 146 is sent to alcohol conversion unit 148, where the alcohol is converted into a hydrocarbon or ether. In one embodiment, this is achieved by dehydrating the methanol to produce dimethyl ether, which itself can be used as a fuel (output from ether fuel output 153), and optionally further dehydrating the dimethyl ether to produce the hydrocarbon. In this embodiment, the methanol may be polymerized in the presence of a zeolite (i.e., aluminosilicate such as ZSM-5) catalyst to yield hydrocarbon fuels. Using this process, the polymerized methanol may yield hydrocarbons where 80% of the hydrocarbon molecules include five or more carbon atoms. In some embodiments, these hydrocarbon molecules may be separated by molecular weight and/or structure prior to being output by hydrocarbon fuel output 152.

Figure 1B:
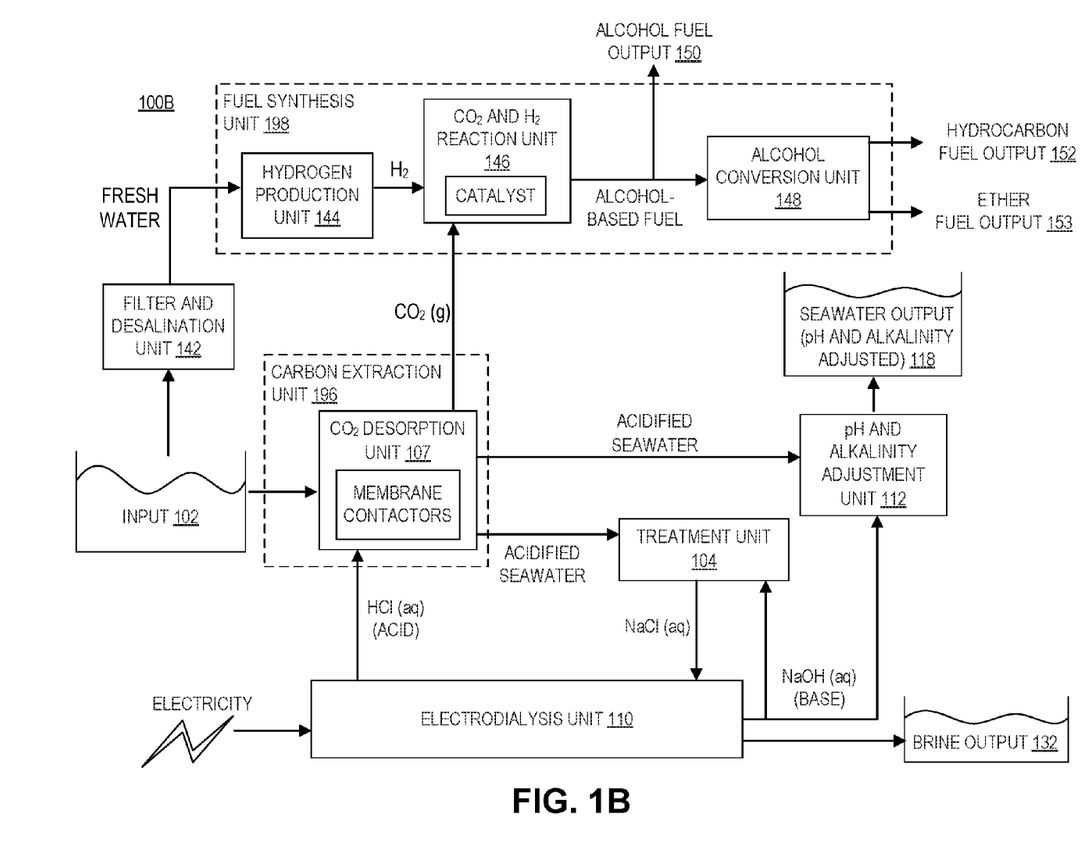
FIG. 1B is an illustration of a system for fuel synthesis, in accordance with an embodiment of the disclosure.

FIG. 1B is an illustration of system 100B for fuel synthesis, in accordance with an embodiment of the disclosure. System 100B is similar in many respects to system 100A; however, carbon extraction unit 196 includes $CO_2$ desorption unit 107 in lieu of precipitation unit 106 and acidification unit 108. System 100B is also lacking $CaCl_2$ output 118 since acidification of calcium salts is not necessary in system 100B.

In the depicted embodiment, electrodialysis unit 110 is coupled to receive aqueous NaCl, and to output aqueous HCl and aqueous NaOH. Degasification unit 107 has a first input coupled to receive an aqueous solution including dissolved inorganic carbon, and a second input coupled to electrodialysis unit 110 to receive the aqueous HCl. In response to receiving the aqueous solution and the aqueous HCl, degasification unit 107 evolves $CO_2$ from the aqueous solution and outputs the aqueous solution. As shown, the aqueous solution may include seawater, and the aqueous NaCl may also be derived, at least in part, from seawater. Degasification unit 107 may include membrane contactors to remove dissolved $N_2$ and $O_2$ gas from the aqueous solution, prior to evolving the $CO_2$ from the aqueous solution. It is worth noting that in other embodiments, other gases may be extracted from the aqueous solution. Furthermore, any of the processes described above may be vacuum assisted.

Figure 1C:
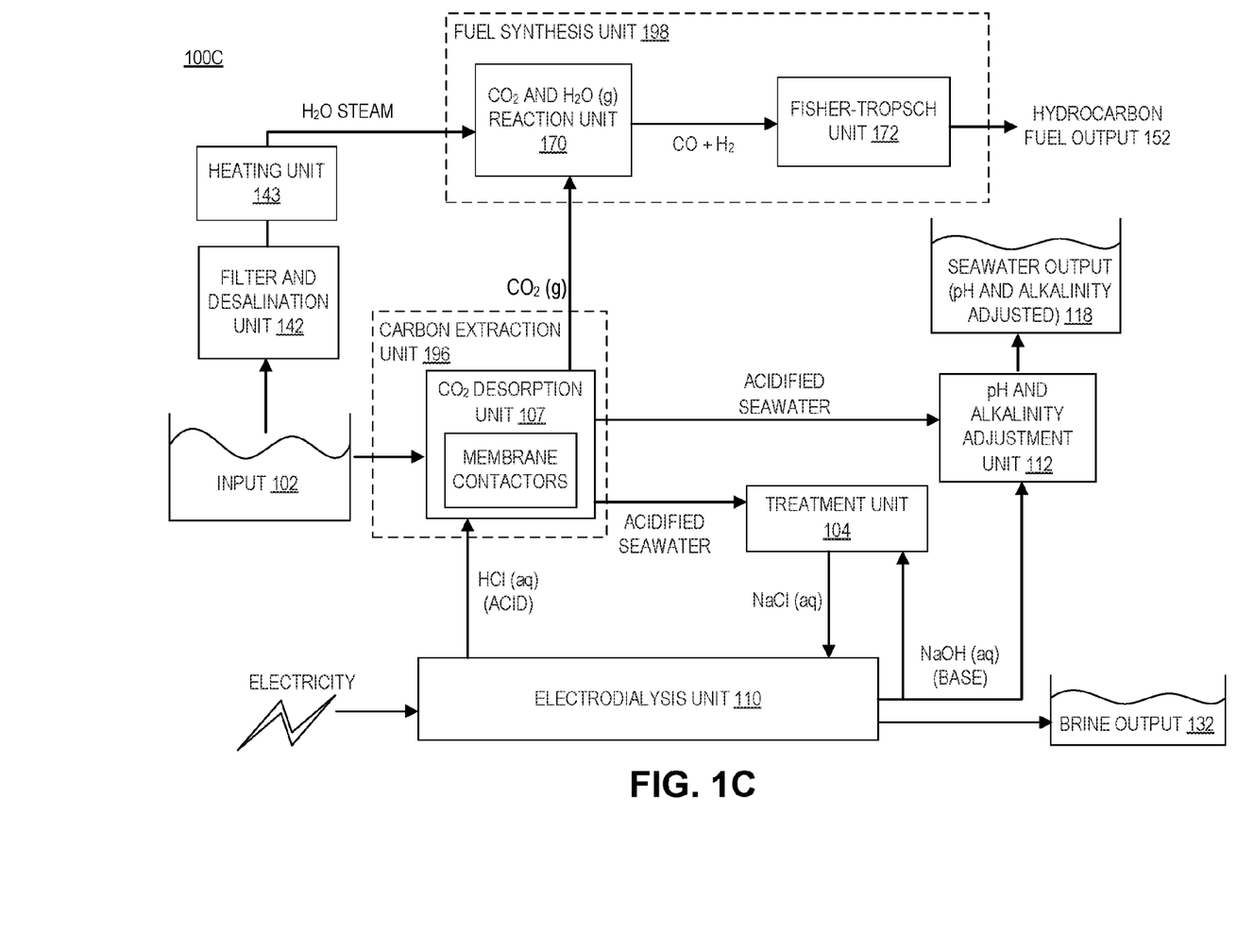
FIG. 1C is an illustration of a system for fuel synthesis, in accordance with an embodiment of the disclosure.

FIG. 1C is an illustration of system 100C for fuel synthesis, in accordance with an embodiment of the disclosure. System 100C is similar in many respects to system 100B; however, fuel synthesis unit 198 includes: $CO_2$ and $H_2O$ reaction unit 170 and Fisher-Tropsch unit 172, in lieu of hydrogen production unit 144, $CO_2$ and $H_2$ reaction unit 146, alcohol conversion unit 148, ether fuel output 153, and alcohol fuel output 150. System 100C also includes heating unit 143.

In the depicted embodiment, fuel synthesis unit 198 receives gaseous fresh water from filter and desalination unit 142 and heating unit 143. This may be advantageous because filter and desalination unit 142 and heating unit 143 merely need to boil water to separate minerals and unwanted aggregate from the steam that filter and desalination unit 142 outputs. The gaseous fresh water from filter and desalination unit 142, and $CO_2$ from carbon extraction unit 196 is then received by $CO_2$ and $H_2O$ reaction unit 170. In one embodiment, $CO_2$ and $H_2O$ reaction unit 170 converts the $CO_2$ to CO for syngas. In one embodiment (not depicted in FIG. 1C), the syngas may then be reacted in the presence of a catalyst (e.g., copper and zinc oxides, supported on alumina) to produce methanol.

In the depicted embodiment, the syngas is sent to Fisher-Tropsch unit 172, which reacts the CO with hydrogen to produce the hydrocarbon. The growth of hydrocarbon chains via Fisher-Tropsch reactions involves repeat steps where hydrogen atoms are added to both carbon and oxygen atoms. The C/O-bond is split and a C/C-bond forms ($CO+2H_2 \rightarrow (CH_2)_n+H_2O$). The hydrogenated molecules formed may be separated both molecular weight and structure to yield pure fuels (e.g., octane).

Systems 100A-100C may be coupled to, and run by, electronic control systems. Regulation and monitoring may be accomplished by a number of sensors throughout the system that either send signals to a controller or are queried by controller. For example, with reference to electrodialysis unit 110, monitors may include one or more pH gauges to monitor a pH within the units as well as pressure sensors to monitor a pressure among the compartments in electrodialysis unit 110 (to avoid inadvertent mechanical damage to electrodialysis unit 110). Another monitor may be a pH gauge placed within precipitation unit 106 to monitor a pH within the tank. The signals from such pH monitor or monitors allows a controller to control a flow of brine solution (from input 102) and a basified solution (from electrodialysis unit 110) to maintain a pH value of a combined solution that will result in a precipitation of $CaCO_3$.

Alternatively, systems 100A-100C may be controlled manually. For example, a worker may open and close valves to control the various water, acid, and base flows in systems 100A-100C. Additionally, a worker may remove precipitated calcium salts from precipitation unit 106. However, one skilled in the relevant art will appreciate that systems 100A-100C may be controlled by a combination of manual labor and mechanical automation, in accordance with the teachings of the present disclosure. Further, all components in systems 100A-100C are interchangeable between the various embodiments, and may be directly coupled to one another.

Figure 2:
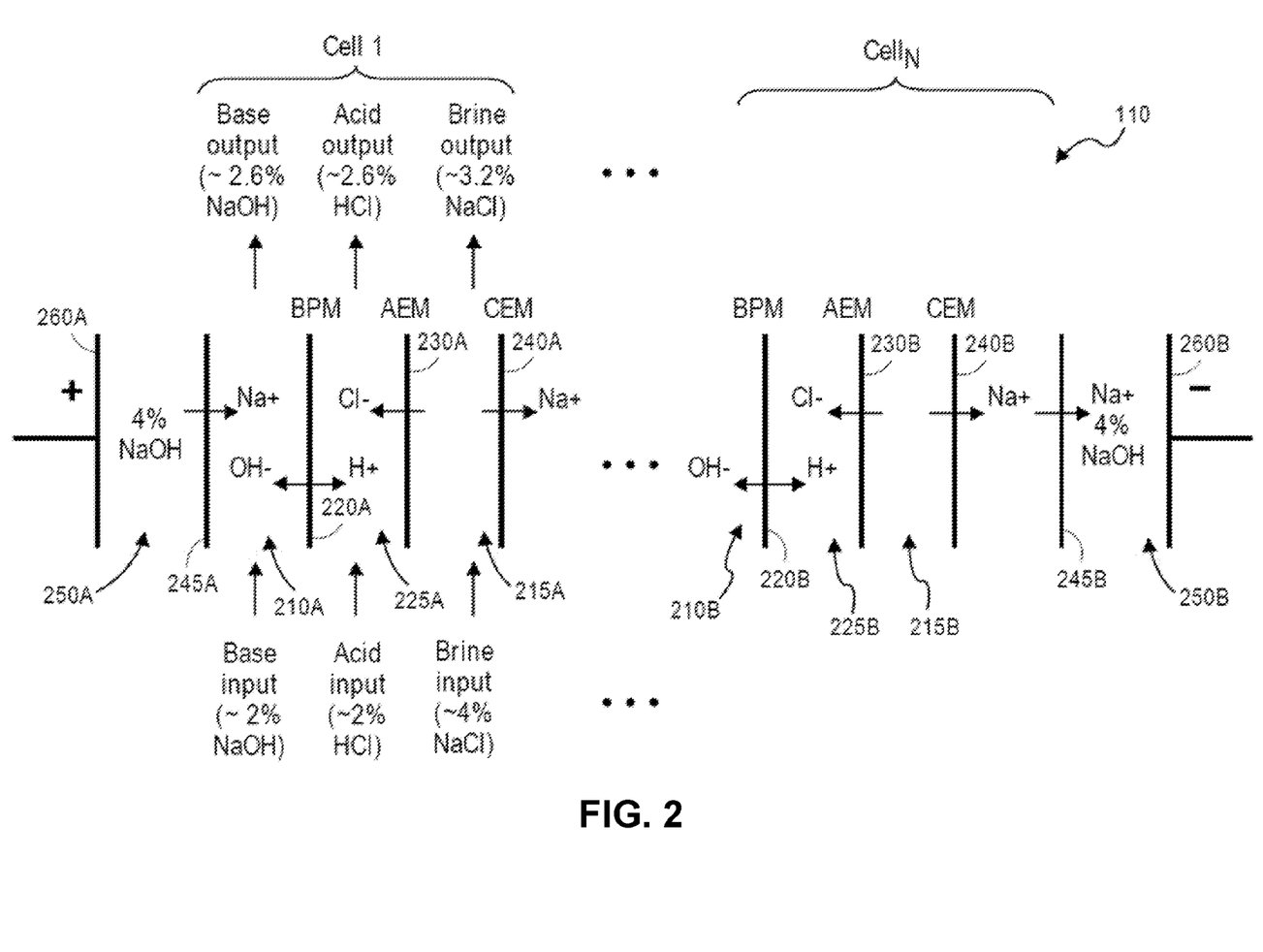
FIG. 2 is an example electrodialysis unit, in accordance with an embodiment of the disclosure.

FIG. 2 is an example electrodialysis unit 110 (e.g., electrodialysis unit 110 of FIG. 1A-1C), in accordance with an embodiment of the disclosure. Electrodialysis unit 110 may be used to convert seawater (or other NaCl-containing aqueous solutions) into NaOH and HCl. As shown, in FIGS. 1A-1C, NaOH and HCl may be used to adjust the pH of the aqueous solution to evolve $CO_2$ gas. In one embodiment, electrodialysis unit 110 is a bipolar membrane electrodialysis unit.

In the depicted embodiment, electrodialysis unit 110 representatively consists of several cells in series, with each cell including a basified solution compartment (compartments 210A and 210B illustrated); an acidified solution compartment (compartments 225A and 225B illustrated); and a brine solution compartment (compartments 215A and 215B). FIG. 2 also shows a bipolar membrane (BPM) between a basified solution compartment and an acidified solution compartment (BPM 220A and 220B illustrated). A suitable BPM is a Neosepta BP-1E, commercially available from Ameridia Corp. Also depicted are anion exchange membranes (AEM), such as Neosepta ACS (commercially available from Ameridia Corp.), disposed between a brine compartment and an acidified solution compartment (AEM 230A and 230B illustrated). A cation exchange membrane (CEM) such as Neosepta CMX-S (commercially available from Ameridia Corp.), is disposed adjacent to a brine compartment (CEM 240A and CEM 240B illustrated). Finally, FIG. 2 shows end cap membranes 245A and 245B (such as Nafion® membranes) that separate the membrane stack from electrode solution compartment 250A and electrode solution compartment 250B, respectively.

Broadly speaking, under an applied voltage provided to electrodialysis unit 110, water dissociation inside the BPM (and the ion-selective membranes comprising a BPM) will result in the transport of hydrogen ions (H+) from one side of the BPM, and hydroxyl ions (OH—) from the opposite side. AEMs/CEMs, as their names suggest, allow the transport of negatively/positively charged ions through the membrane. The properties of these membranes such as electrical resistance, burst strength, and thickness are provided by the manufacturer (e.g., Neosepta ACS and CMX-S are monovalent-anion and monovalent-cation permselective membranes, respectively). In one embodiment, electrodialysis unit 110 includes electrodes 260A and 260B of, for example, nickel manufactured by De Nora Tech Inc. FIG. 2 also shows electrode solution compartment 250A and electrode solution compartment 250B through which, in one embodiment, a NaOH(aq) solution is flowed. Where electrode 260A is a positively-charged electrode, sodium ions (Na+) will be encouraged to move across cap membrane 245A and where electrode 260B is negatively-charged, sodium ions will be attracted to electrode solution compartment 250B. In one embodiment, the solution compartments between adjacent membranes are filled with polyethylene mesh spacers (e.g., 762 μm thick polyethylene mesh spacers), and these compartments are sealed against leaks using axial pressure and 794 mm thick EPDM rubber gaskets.

Figure 3:
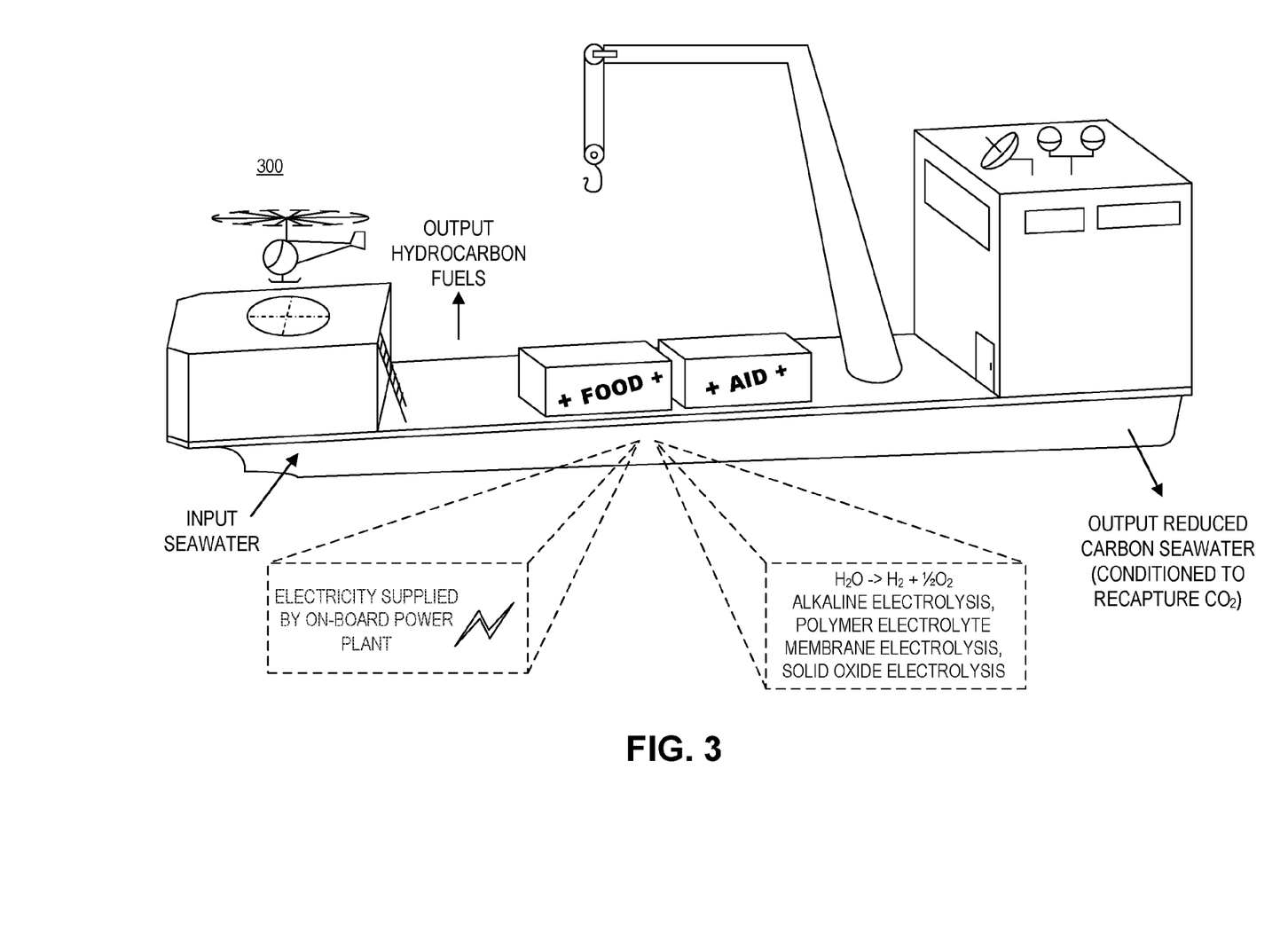
FIG. 3 is an example application of a system for fuel synthesis, in accordance with an embodiment of the disclosure.

FIG. 3 is an example application of system 300 for fuel synthesis, in accordance with an embodiment of the disclosure. As depicted, system 300 (e.g., systems 100A-100C) for fuel synthesis is included on a large commercial vessel (which may include a ship, oil rig, or the like). Here, the vessel is able to create alcohol/ether/hydrocarbon fuels using an on-board power plant. In one embodiment, a nuclear reactor is used to power electrolysis equipment to generate the necessary acids and bases to create the alcohol, ether, or hydrocarbon based fuels. These fuels may be used by helicopters and other aircraft for delivering food and aid supplies, or for other reasons, such as refueling ships at sea.

Figure 4:
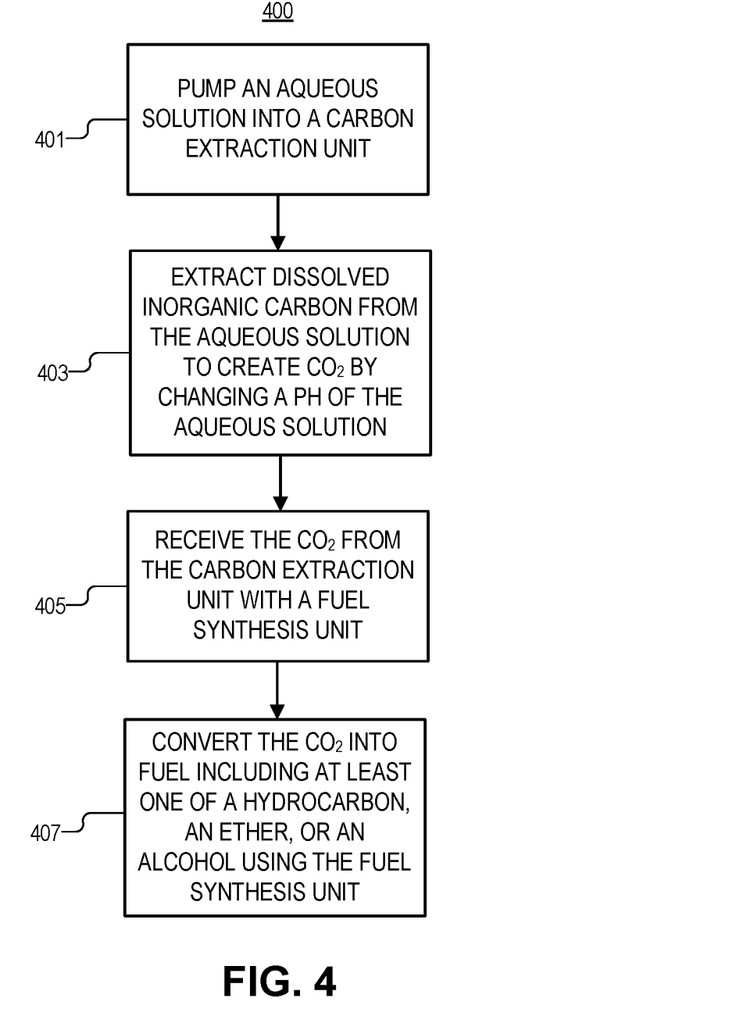
FIG. 4 is an illustration of a method for synthesizing fuel from an aqueous solution, in accordance with an embodiment of the disclosure.

FIG. 4 is an illustration of method 400 for synthesizing fuel from an aqueous solution, in accordance with an embodiment of the disclosure. The order in which some or all of process blocks 401-407 appear in method 400 should not be deemed limiting. Rather, one of ordinary skill in the art having the benefit of the present disclosure will understand that some of method 400 may be executed in a variety of orders not illustrated, or even in parallel. Additionally, method 400 may include additional blocks or have fewer blocks than shown, in accordance with the teachings of the present disclosure.

Block 401 illustrates pumping the aqueous solution, containing dissolved inorganic carbon, from a body of water into a carbon extraction unit. In one embodiment, the aqueous solution includes seawater containing bicarbonate ions ($HCO_3^-$).

Block 403 discloses extracting the dissolved inorganic carbon from the aqueous solution to create $CO_2$ by changing a pH of the aqueous solution in the carbon extraction unit. In one embodiment, extracting the dissolved inorganic carbon includes increasing the pH of the aqueous solution to precipitate salts containing carbon, and applying acid to the salts to evolve $CO_2$ gas. This may involve adding aqueous NaOH to the aqueous solution, and adding aqueous HCl to the salts to evolve the $CO_2$. In an alternate embodiment, extracting the dissolved inorganic carbon includes decreasing the pH of the aqueous solution (e.g., with HCl) to remove $CO_2$ gas from the aqueous solution.

Block 405 shows receiving the $CO_2$ from the carbon extraction unit with a fuel synthesis unit. In several embodiments, the fuel synthesis unit may include devices to drive chemical reactions between the $CO_2$ and hydrogen containing materials (e.g., $H_2$, $H_2O$, or the like). To supply $H_2$, water may be decomposed into hydrogen and oxygen via at least one of alkaline electrolysis, polymer electrolyte membrane electrolysis, or solid oxide electrolysis. To facilitate fuel-building reactions, fuel synthesis unit may contain a number of different metal oxide catalysts, chambers, pipes, pumps, etc.

Block 407 illustrates converting the $CO_2$ into fuel including at least one of a hydrocarbon, ether, or an alcohol using the fuel synthesis unit. Conversion of $CO_2$ may yield methanol or higher order alcohols (e.g., ethyl alcohol, butyl alcohol, isopropyl alcohol, or the like) and/or the creation of linear hydrocarbons/ethers such as (methane, ethane, propane, butane, pentane, hexane, octane, and oxygen-substituted ether equivalents) as well as branched and cyclical derivatives (e.g., isopentane, cyclohexane, to name a few). In one embodiment, reacting the $CO_2$ with the hydrogen includes reacting gaseous water (hydrogen containing material) and the $CO_2$ to produce CO, hydrogen, and $O_2$; the CO and the hydrogen are reacted in the presence of a catalyst to produce methanol. In another embodiment, converting the $CO_2$ into the fuel includes reacting gaseous water and the $CO_2$ to produce CO, hydrogen, and $O_2$, and using the CO and the hydrogen to perform a Fisher-Tropsch reaction to produce hydrocarbons. This may involve feeding gaseous water and $CO_2$ into a solid oxide electrolysis cell to produce syngas. One skilled in the art will realize that there are many different reactions to yield alcohols and hydrocarbons from $CO_2$. Furthermore, the reactions discussed above may yield any number of synthetic byproducts depending on the processing conditions. All of these byproducts may be sorted by chemical structure and molecular weight to achieve commonly employed fuels (e.g., n-octane) and fuel additives.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method of synthesizing fuel from an aqueous solution, comprising:
pumping the aqueous solution containing dissolved inorganic carbon from a body of water into a carbon extraction unit;
extracting the dissolved inorganic carbon from the aqueous solution to create $CO_2$ by changing a pH of the aqueous solution in the carbon extraction unit using an electrodialysis unit coupled to the carbon extraction unit, wherein in response to receiving the aqueous solution with a brine solution compartment disposed in the electrodialysis unit, the electrodialysis unit outputs at least one of aqueous NaOH or aqueous HCl to the carbon extraction unit;
receiving the $CO_2$ from the carbon extraction unit with a fuel synthesis unit coupled to the carbon extraction unit; and
converting the $CO_2$ into the fuel including at least one of a hydrocarbon, an alcohol, or an ether using the fuel synthesis unit.

2. The method of claim 1, wherein converting the $CO_2$ into the fuel includes reacting the $CO_2$ with hydrogen to produce the alcohol, and wherein the alcohol includes methanol.

3. The method of claim 2, further comprising decomposing water into the hydrogen and oxygen, in a hydrogen production unit included in the fuel synthesis unit and coupled to receive the aqueous solution, using at least one of alkaline electrolysis, polymer electrolyte membrane electrolysis, or solid oxide electrolysis.

4. The method of claim 2, wherein reacting the $CO_2$ with the hydrogen includes decomposing water in the aqueous solution into the hydrogen and oxygen, and reacting the hydrogen and the $CO_2$ in the presence of a catalyst to produce the methanol.

5. The method of claim 2, further comprising at least one of dehydrating the methanol to produce dimethyl ether, or dehydrating the methanol to produce the dimethyl ether and dehydrating the dimethyl ether to produce the hydrocarbon.

6. The method of claim 2, wherein reacting the $CO_2$ with the hydrogen includes:
reacting gaseous water and the $CO_2$ to produce CO the hydrogen, and $O_2$; and
reacting the CO and the hydrogen in the presence of a catalyst to produce the methanol.

7. The method of claim 1, wherein converting the $CO_2$ into the fuel includes:
reacting gaseous water and the $CO_2$ to produce CO, hydrogen, and $O_2$; and
using the CO and the hydrogen to perform a Fisher-Tropsch reaction to produce the hydrocarbon.

8. The method of claim 7; wherein reacting the gaseous water and the $CO_2$ includes feeding the gaseous water and the $CO_2$ into a solid oxide electrolysis cell.

9. The method of claim 1, wherein extracting the dissolved inorganic carbon includes:
increasing the pH of the aqueous solution to precipitate salts containing carbon, wherein the aqueous solution includes seawater; and
applying acid to the salts to evolve $CO_2$ gas.

10. The method of claim 9, wherein increasing the pH includes adding aqueous NaOH to the aqueous solution, and wherein applying the acid to the salts includes applying the aqueous HCl to the salts.

11. The method of claim 1, wherein extracting the dissolved inorganic carbon includes decreasing the pH of the aqueous solution to remove $CO_2$ gas from the aqueous solution, wherein the aqueous solution includes seawater.

12. The method of claim 1, further comprising filtering the aqueous solution, with a treatment unit coupled to the electrodialysis unit to remove ions and organic matter from the water.

13. The method of claim 1, wherein the electrodialysis unit is coupled to perform operations comprising:
receiving the aqueous solution with the brine solution compartment disposed in the electrodialysis unit;
applying a voltage across electrodes in the electrodialysis unit;
outputting the aqueous solution from the brine solution compartment with a lower salt concentration in response to the voltage applied across the electrodes;
receiving the aqueous HCl with an acidified solution compartment disposed in the electrodialysis unit;
applying the voltage across the electrodes in the electrodialysis unit; and
outputting the aqueous HCl, with a higher HCl concentration, from the acidified solution compartment, wherein chlorine ions in the brine solution compartment traveled to the acidified solution compartment in response to the voltage cross the electrodes.

14. The method of claim 13, wherein the electrodialysis unit is coupled to perform operations further comprising:
receiving the aqueous NaOH with a basified solution compartment disposed in the electrodialysis unit;
applying the voltage across the electrodes in the electrodialysis unit; and
outputting the aqueous NaOH from the basified solution compartment with a higher NaOH concentration in response to the voltage applied across the electrodes.

15. The method of claim 14, wherein in response to the voltage, the chlorine ions flow through an anion exchange membrane disposed between the brine solution compartment and the acidified solution compartment, and wherein in response to the voltage, hydrogen ions and hydroxyl ions flow through a bipolar membrane disposed between the acidified solution compartment and the basified solution compartment.

16. The method of claim 15, wherein applying the voltage across the electrodes in the electrodialysis unit includes collecting sodium ions at a negatively charged terminal, and wherein the brine solution compartment, the acidified solution compartment, and the basified solution compartment are included in a first cell in a plurality of cells in the electrodialysis unit.

17. The method of claim 1, further comprising neutralizing the aqueous solution, in a pH and alkalinity adjustment unit coupled to the electrodialysis unit, with the aqueous NaOH or the aqueous HCl, after extracting the dissolved inorganic carbon from the aqueous solution.

18. The method of claim 3, wherein the hydrogen production unit and the carbon extraction unit are coupled to a $CO_2$ and $H_2$ reaction unit included in the fuel synthesis unit.

19. The method of claim 18, further comprising desalinating at least part of the aqueous solution to produce the water using a filter and desalination unit coupled to the hydrogen production unit.

20. The method of claim 18, wherein converting the $CO_2$ into the fuel occurs on a ship.

* * * * *

UNITED STATES PATENT AND TRADEMARK OFFICE
CERTIFICATE OF CORRECTION

PATENT NO. : 9,914,683 B2
APPLICATION NO. : 15/165357
DATED : March 13, 2018
INVENTOR(S) : Eisaman Page 1 of 1

It is certified that error appears in the above-identified patent and that said Letters Patent is hereby corrected as shown below:

In the Claims

| Column | Line | Error |
| --- | --- | --- |
| 10 (Claim 10) | 6 | "adding aqueous NaOH" should read --adding the aqueous NaOH-- |
| 10 (Claim 12) | 17 | "the water" should read --the sea water-- |

Signed and Sealed this
Twenty-fourth Day of July, 2018

Andrei Iancu
*Director of the United States Patent and Trademark Office*